(12) United States Patent
Atkinson et al.

(10) Patent No.: US 9,302,074 B2
(45) Date of Patent: Apr. 5, 2016

(54) NASAL RETENTION SYSTEM INCLUDING A SPLIT BALL CLIP

(75) Inventors: Gordon E. Atkinson, Hickory, NC (US); Kyle S. Adams, Dallas, TX (US)

(73) Assignee: iMed Technology, Inc., Dallas, TX (US)

( * ) Notice: Subject to any disclaimer, the term of this patent is extended or adjusted under 35 U.S.C. 154(b) by 949 days.

(21) Appl. No.: 13/533,089

(22) Filed: Jun. 26, 2012

(65) Prior Publication Data

US 2013/0340764 A1 Dec. 26, 2013

(51) Int. Cl.
*A61M 5/32* (2006.01)
*A61M 25/02* (2006.01)

(52) U.S. Cl.
CPC ......... *A61M 25/02* (2013.01); *A61M 2025/024* (2013.01); *A61M 2025/028* (2013.01); *A61M 2025/0226* (2013.01); *A61M 2209/088* (2013.01); *A61M 2210/0618* (2013.01)

(58) Field of Classification Search
CPC ............ A61J 15/0034; A61J 15/0061; A61M 2210/0618; A61M 25/02; A61M 2025/0226; A61M 2025/024; A61M 2209/088; A61M 5/1418
See application file for complete search history.

(56) References Cited

U.S. PATENT DOCUMENTS

| 4,114,626 | A | 9/1978 | Beran |
| 4,778,448 | A | 10/1988 | Meer |
| 4,823,789 | A | 4/1989 | Beisang, III |
| 5,105,807 | A | 4/1992 | Kahn et al. |
| 5,185,005 | A | 2/1993 | Ballantyne |
| 5,398,679 | A | 3/1995 | Freed |
| 5,613,655 | A | 3/1997 | Marion |
| 6,029,668 | A | 2/2000 | Freed |
| 6,631,715 | B2 | 10/2003 | Kirn |
| 6,837,237 | B2 | 1/2005 | Kirn |
| 7,534,228 | B2 | 5/2009 | Williams |
| 2009/0139061 | A1 | 6/2009 | Nishtala |
| 2009/0162816 | A1* | 6/2009 | Charles ................ A44C 5/0015 434/127 |

* cited by examiner

*Primary Examiner* — Emily Schmidt
(74) *Attorney, Agent, or Firm* — Stevens & Showalter, LLP

(57) ABSTRACT

A nasal retention system for securing a nasal tube extending through a nose of a patient. The retention system comprises a clip member formed of a soft elastomeric material and including first and second pivotally connected clip portions. Each of the clip portions have a generally hemispherical shape such that a generally spherical shape is defined when the clip portions are pivoted together. The first clip portion includes an elongated nasal tube channel extending into the first clip portion, and extending between diametrically opposite sides of a perimeter of the first clip portion. The elongated channel receives a nasal tube therethrough when mating surfaces of the two clip portions are in mating engagement with each other.

16 Claims, 5 Drawing Sheets

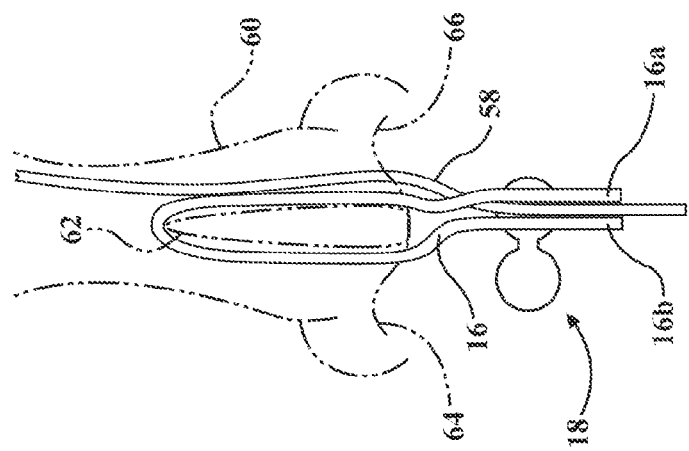
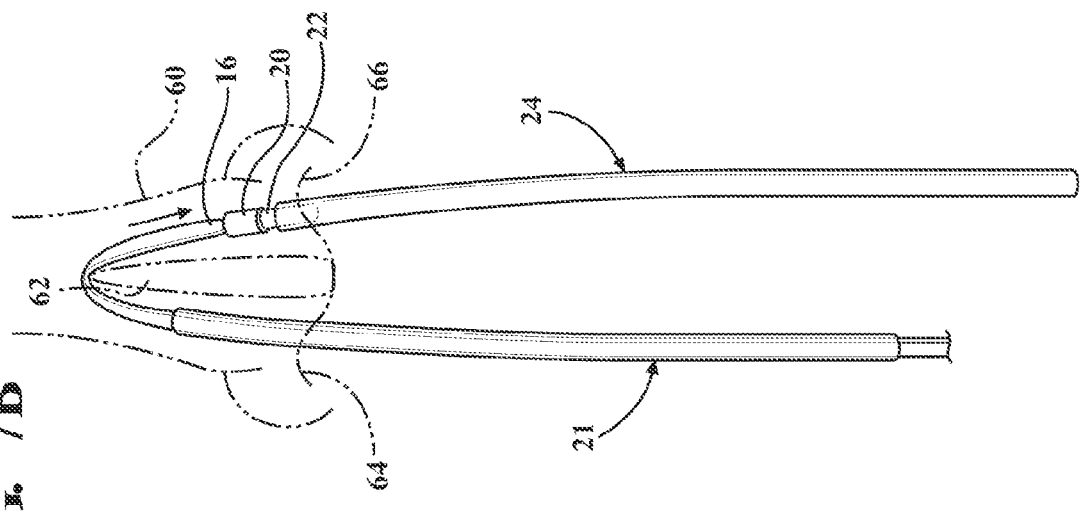
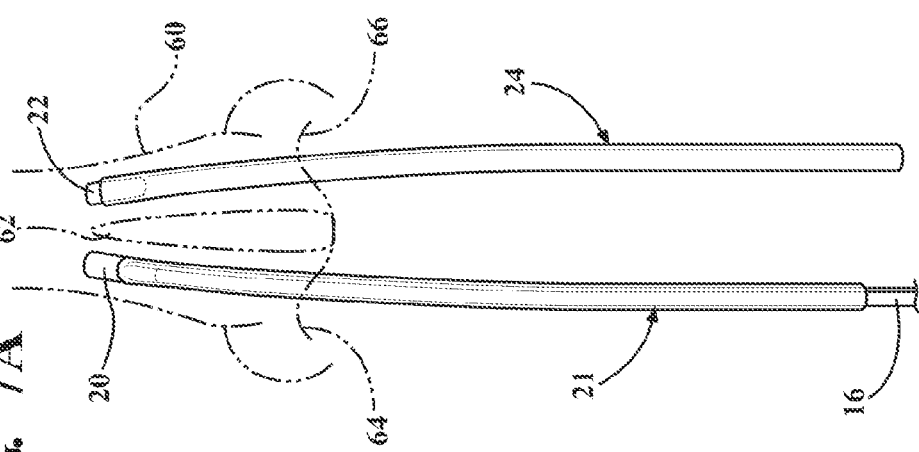

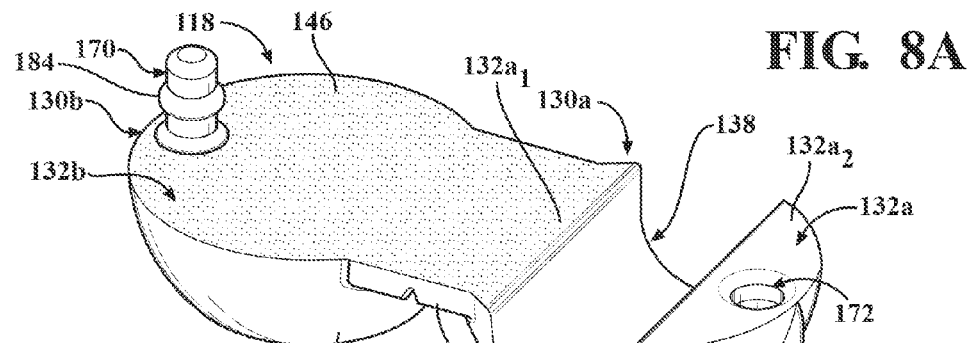
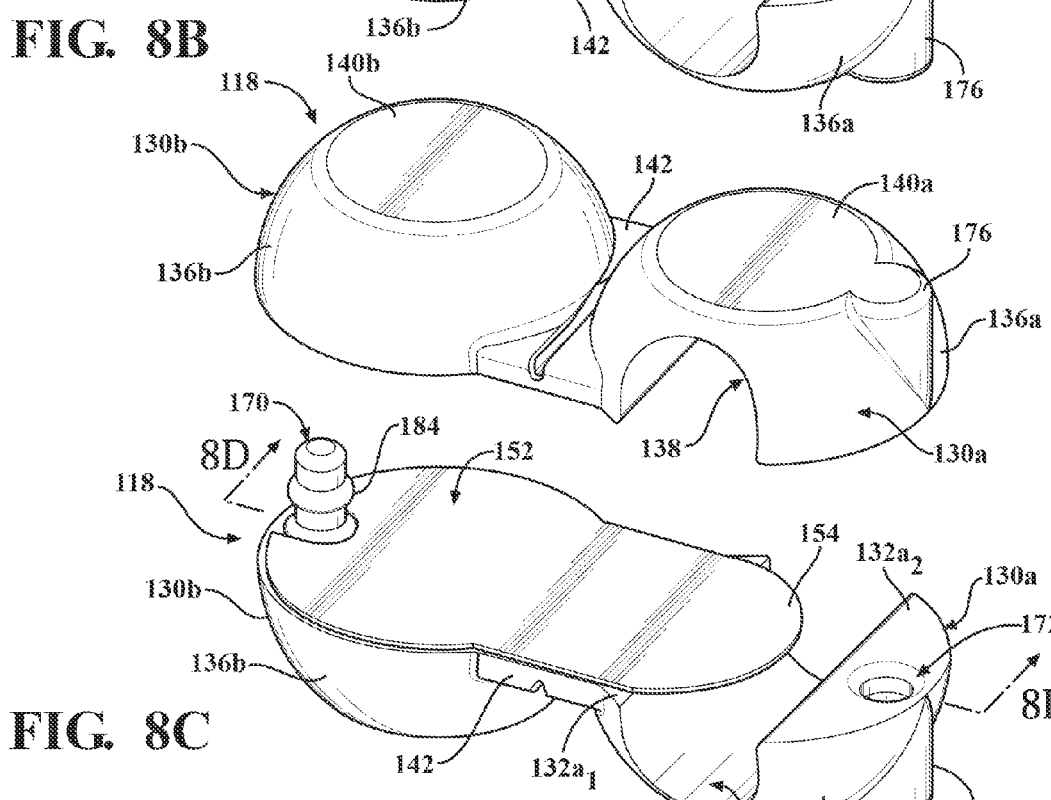
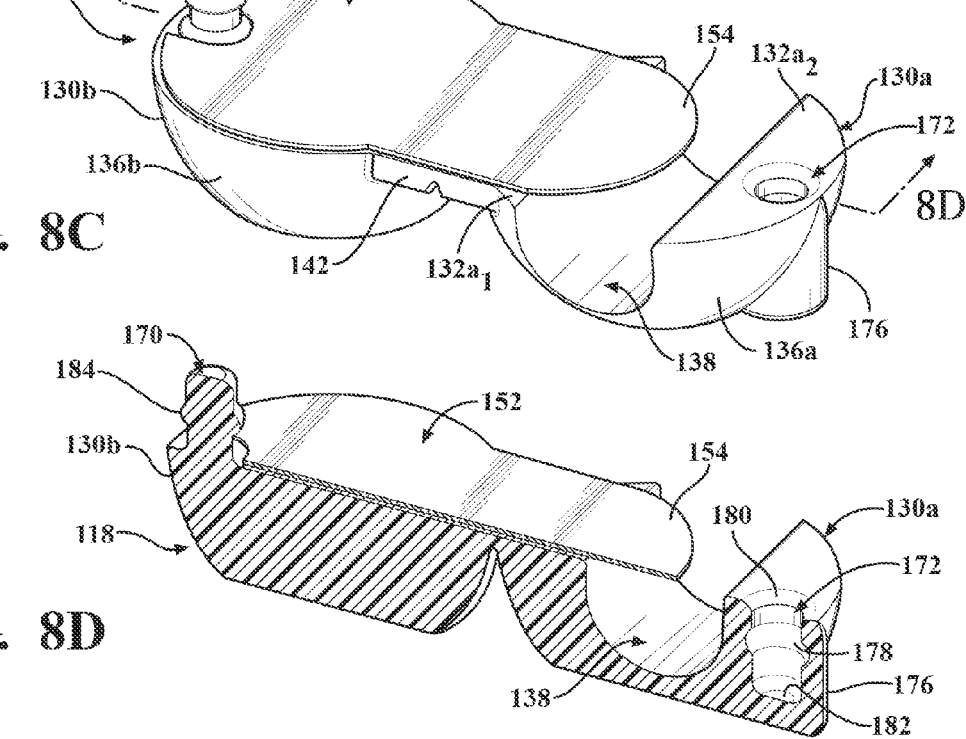
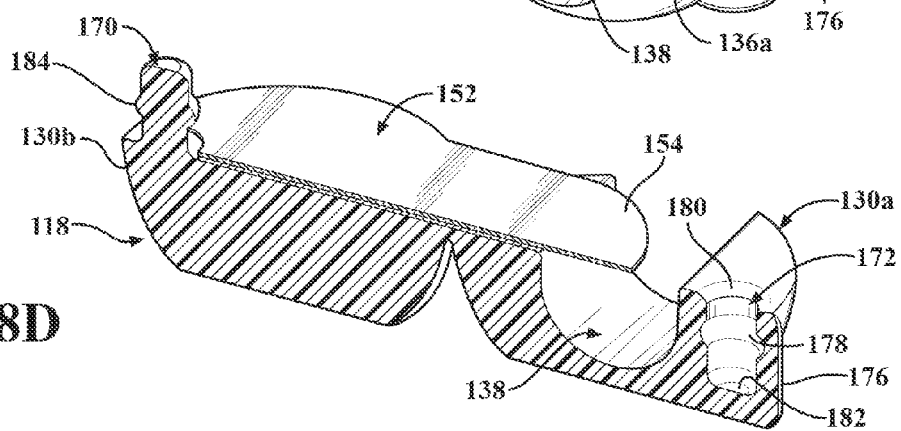

NASAL RETENTION SYSTEM INCLUDING A SPLIT BALL CLIP

FIELD OF THE INVENTION

The present invention relates to nasal tube retention systems and, more particularly, to a clip member for retaining a nasal tube in a desired location within a patient.

BACKGROUND OF THE INVENTION

A tubing inserted through the nasal passage of a medical patient may be provided to introduce fluids into the gastrointestinal tract of the patient. A securing system is required to support and maintain placement of the tubing once it is inserted through the nasal passage and appropriately positioned to achieve the desired treatment. Treatments administered to the patient by the nasal tube method can require that the tubing remain in place for extended periods of time. Hence, it is particularly important to provide a means of securing nasal tubing in a particular position for extended periods while providing maximum comfort for the patient.

Typically, the nasal tube securing system may use tape or may include a cord that passes around the patient's posterior nasal septum. The ends of the cord extend from the nostrils of the patient and may be secured to the nasal tube by an anchoring clip member. The anchoring clip member is positioned just below the nose of the patient and may become a source of irritation to the patient due to contact and/or movement between the clip member and the portion of patient's face adjacent to the clip member.

SUMMARY OF THE INVENTION

In accordance with an aspect of the invention, a nasal retention system is provided for securing at least one nasal tube extending through a nose of a patient. The retention system comprises a clip member including first and second pivotally connected clip portions, each of the clip portions including a planar inner mating surface for mating engagement with the planar mating surface of the other clip portion. The planar mating surface of each of the clip portions defines a generally circular perimeter at an intersection of the planar mating surface with an outer surface of the clip portion. The first clip portion includes an elongated nasal tube channel extending from the planar surface into the first clip portion. The elongated nasal tube channel extends between diametrically opposite sides of the perimeter of the first clip portion for receiving a nasal tube therethrough when the mating surfaces are in mating engagement with each other.

In accordance with further aspects of the invention, the clip portions may be formed of a relatively soft elastomeric material that flexes resiliently in response to pressure applied to a surface thereof. The soft elastomeric material may be an elastomeric material in a durometer Shore A range of 40 or less. The outer surface of each of the first and second clip portions may be defined as a generally hemispherical outer surface. The clip member, with the mating surfaces in mating engagement, may define a generally spherical member of a size to prevent entry into a patient's nostril. The clip portions may include diametrically opposed flat portions formed on each of the generally hemispherical portions defining opposed finger engagement locations. A diameter defined by an outer surface of the generally spherical member may be about ½ inch. At least one of the first and second clip portions may include an adhesive coating for retaining the clip portions in engagement with each other upon contact of the mating surfaces with each other. A pin may be located on one of the first and second clip portions and a hole may be located on the other of the first and second clip portions, the pin and hole may be located for engagement with each to maintain the clip portions in engagement with each other when the mating surfaces are in mating engagement with each other. The elongated nasal tube channel may have a radially inner surface, located radially inwardly from the mating surface of the first clip portion, and the radially inner surface may define a radius generally equal to one-half an outer diameter of the nasal tube received therein. A depth of the elongated nasal tube channel, extending into the first clip portion from the mating surface, may be generally equal to a width of the channel. Engagement surfaces on the mating surfaces may be provided for engaging a nasal retention umbilical tape on either side of the elongated nasal tube channel.

In accordance with another aspect of the invention, a nasal retention system is provided for securing at least one nasal tube to a nose of a patient. The nasal retention system is provided in combination with a nasal tube extending into a nostril of the nose of the patient, a support cord extending around a nasal septum of the patient and having opposing ends, each cord end extending from a nostril of the nose, and including a clip member engaged with the tube and engaged with the ends of the support cord. The clip member includes first and second pivotally connected clip portions formed of a soft elastomeric material, each of the clip portions including an interior surface defining a planar inner mating surface for mating engagement with the planar mating surface of the other clip portion. The planar mating surface of each the clip portions defines a generally circular perimeter at an intersection of the planar mating surface with an outer surface the clip portion. The first clip portion includes an elongated nasal tube channel extending from the planar surface into the clip first clip portion. The elongated nasal tube channel extends between diametrically opposite sides of the perimeter of the first clip portion for receiving the nasal tube therethrough. At least a portion of the second clip interior surface engages the nasal tube, and a portion of the interior surfaces of each of the first and second clip portions engage the ends of the support cord, when the mating surfaces are in mating engagement with each other in an assembled state.

In accordance with further aspects of the invention, the mating surface of the second clip portion may include an adhesive coating for retaining the clip portions in engagement with each other upon contact of the mating surfaces with each other, and the ends of the support cord may extend along the mating surfaces, generally parallel to the elongated nasal tube channel, to retain the support cord in engagement between the first and second clip portions. The soft elastomeric material may be an elastomeric material in a durometer Shore A range of 40 or less. Each of the first and second clip portions may define generally hemispherical elements, and the clip member may define a generally spherical shape of a size to prevent entry into a patient's nostril in the assembled state.

In accordance with another aspect of the invention, a method is provided for securing a nasal tube extending through a nose of a patient. The method includes providing a retention system comprising a clip member having first and second pivotally connected generally hemispherical clip portions, each of the clip portions defining a perimeter and including an inner mating surface within the perimeter for mating engagement with the mating surface of the other clip portion, the first clip portion including an elongated nasal tube channel extending from the mating surface into the first clip portion between diametrically opposite sides of the perimeter of the first clip, and wherein at least one of the first and second clip portions include an adhesive coating. The method further includes:

> passing a first end of a support cord having first and second ends into one nostril past the posterior nasal septum, and retrieving the first end through the other nostril such that the first and second ends of the support cord extend from the patient's nostrils exterior to the nose;
>
> positioning the clip member adjacent to the nose with the nasal tube located extending within the nasal tube channel, the clip member formed of a soft elastomeric material forming a stiction connection between the nasal tube channel and the nasal tube; and
>
> pivoting the first and second clip portions together with the first and second ends of the support cord therebetween to secure the mating surfaces of the first and second clip portions in mating engagement with each other.

In accordance with further aspects of the invention, the method may further include providing an insertion member including an insertion tube having a proximal and distal end, and a first magnetic member resting on the distal end and the support cord extending through the insertion tube and attached to the first magnetic member; providing a retrieval member including a retrieval tube having a proximal and distal end, and including a second magnetic member affixed to the distal end of the retrieval tube, at least one of the first and second magnetic members comprising a magnet; inserting the distal end of the insertion member within a first nostril and the distal end of the retrieval member within a second nostril such that the magnetic members at the distal ends are magnetically coupled at a point beyond the posterior nasal septum; pulling the retrieval member and the magnetically coupled support cord around the posterior nasal septum such that the ends of the support cord extend external to each nostril; and inserting the tube into the patient's nostril and securing the tube to the ends by performing the positioning and pivoting steps. The adhesive coating may be located on the mating surface of the second clip portion and may be adhered in engagement with the nasal tube located in the elongated nasal channel when the engagement surfaces are in mating engagement. A detachable film cover may be located on the adhesive coating, for protecting the adhesive coating from inadvertent contact, and the method may include removing the cover prior to pivoting the first and second clip portions together for mating engagement of the mating surfaces. The method may further include placing the ends of the support cord in engagement with the adhesive coating within the clip member.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

FIG. 3A is perspective view of an inner side of a clip member for the retention system;

FIG. 3B is a perspective view of an outer side of the clip member for the retention system;

FIG. 4 is an end elevation view of the clip member for the retention system;

FIGS. 7A-7C illustrate a process of using the nasal retention system of the present invention;

FIG. 8A is perspective view of an inner side of an alternative configuration for the clip member;

FIG. 8B is a perspective view of an outer side of the alternative configuration for the clip member;

FIG. 8C is a perspective view similar to that of FIG. 8A and including a protective film cover; and FIG. 8D is a cross-sectional perspective view taken along line 8D-8D in FIG. 8C.

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
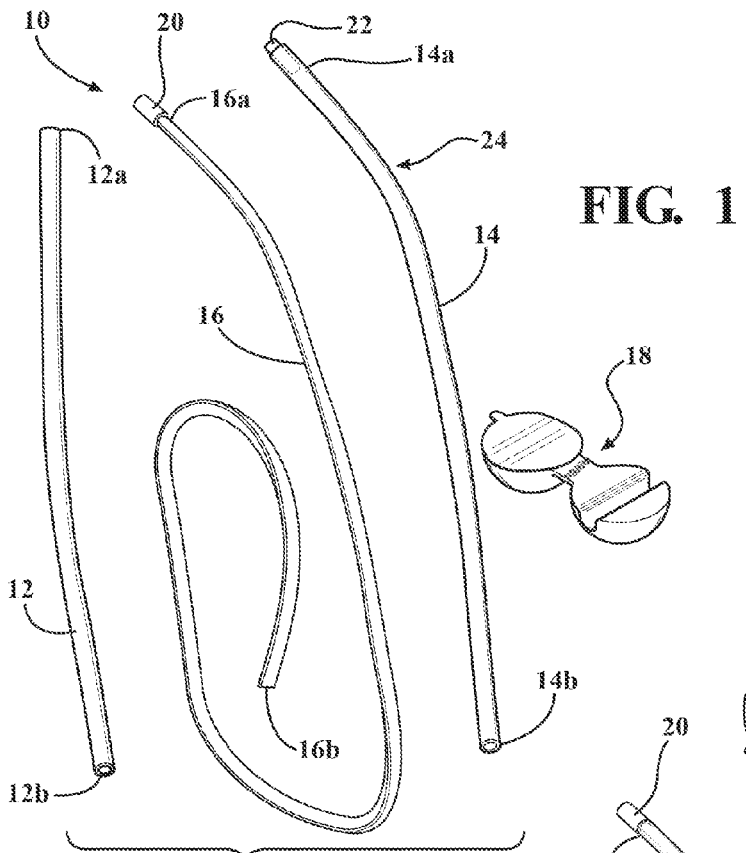
FIG. 1 illustrates the components of a nasal retention system in accordance with aspects of the present invention.

Referring to FIG. 1, in accordance an aspect of the invention, a collection of components or kit is described herein for providing a system 10 for placing and securing a nasal tube, e.g., a nasogastric tube, at a desired position relative to a patient's nose 60 (see FIG. 7A). The system 10 generally includes a first flexible tube or insertion tube 12, a second flexible tube or retrieval tube 14, a support chord 16 having a first cord end 16a and a second cord end 16b, and a clip member 18. The cord 16 preferably comprises an umbilical tape. The cord 16 and the clip member 18 define a nasal retention system wherein the cord 16 is provided for extending around the posterior nasal septum 62 (FIG. 7A) in a patient, to thereby support the nasal tube 58 (see FIG. 7C). The clip member 18 is provided to engage both the cord ends 16a, 16b and the nasal tube 58 to provide support for the nasal tube 58, as will be described further below.

Figure 2:
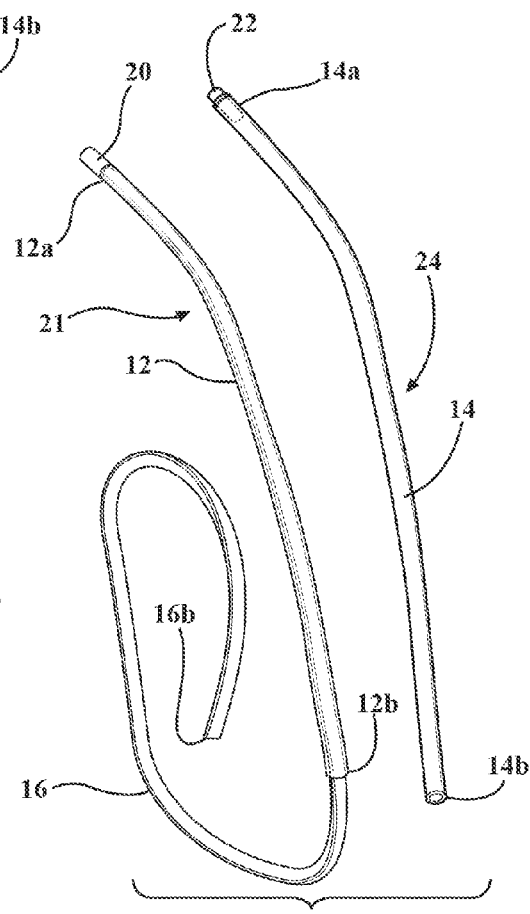
FIG. 2 illustrates an insertion member and a retrieval member for the retention system of FIG. 1.
Figure 5:
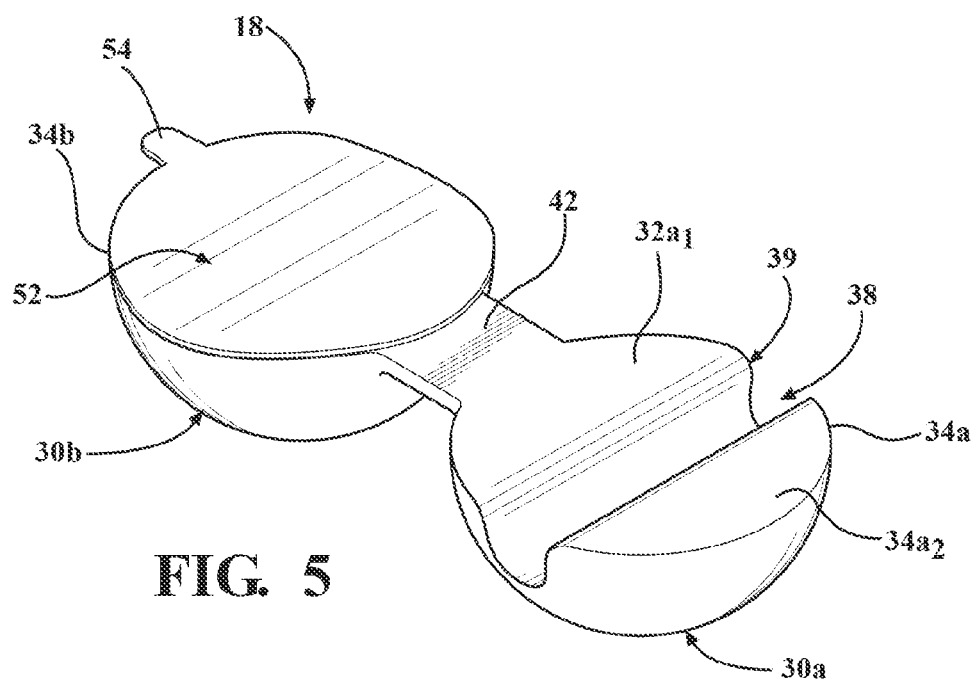
FIG. 5 is a perspective view similar to that of FIG. 3A and including a protective film cover.

Referring to FIGS. 1 and 2, the first end 16a of the cord 16 is attached to a first magnetic member 20 preferably comprising a stainless steel magnetic tip. The attachment between the cord 16 and the first magnetic tip 20 may be accomplished by any conventional means, such as by a mechanical attachment or an adhesive attachment. The cord 16 is initially provided extending through the insertion tube 12 with the first cord end 16a and the first magnetic tip 20 located at a distal end 12a of the insertion tube 12 to form an insertion member 21, as seen in FIG. 2. The first magnetic member 20 may comprise a disc or similar shape and is formed with an outer diameter that is larger than an inner diameter of the first insertion tube 12. Hence, in an initial insertion configuration, the first magnetic member 20 rests on the outer edge of the distal end 12a of the insertion tube 12, and the cord 16 extends through the insertion tube 12 and out past a proximal end 12b of the insertion tube 12. The first magnetic member 20 may be formed of a stainless steel magnetic material.

The retrieval tube 14 includes a distal end 14a and a proximal end 14b. A second magnetic member 22 is non-detachably affixed to the distal end 14b of the retrieval tube 14 to form a retrieval member 24. The second magnetic member 22 may comprise a permanent magnet having a cylindrical shape inserted partially within the retrieval tube 14. The second magnetic member 22 may be retained place within the retrieval tube 14 solely by friction and/or an adhesive may be used to affix the second magnetic member 22 to the retrieval tube 14.

It should be noted that, although the first magnetic member 20 is described herein as being a stainless steel material, other magnetic materials may be provided, and the first magnetic member 20 may comprise a magnet. Similarly, in the event that the first magnetic member 20 comprises a magnet, the second magnetic member 22 may comprise a magnetic material such as a stainless steel material. Also, both of the magnetic members 20, 22 may comprise magnets.

Referring to FIGS. 7A-7C, in accordance with an aspect of a method of the present invention, the insertion and retrieval members 21, 24 are used to pass the first end 16a of the support cord 16 into one nostril past the posterior nasal septum, and retrieve the first end 16a through the other nostril such that the first and second ends 16a, 16b of the support cord 16 extend from the patient's nostrils exterior to the nose. In particular, the distal end 12a of the insertion member 21 is inserted within a first nostril 64, and the distal end 14a of the retrieval member 24 within a second nostril 66 such that the magnetic members 20, 22 at the distal ends 12a, 14a are magnetically coupled at a point beyond the posterior nasal septum 62. That is, the second magnetic member 22 and attached support cord 16 are attracted across the posterior nasal septum 62 to engagement with the first magnetic member 20. The retrieval member 14 is pulled out of the second nostril 66, drawing the magnetically coupled support cord 16 around the posterior nasal septum 62 such that the ends of the support cord 16 extend external to each nostril 64, 66. Subsequently, a nasal tube 58 is inserted into one of the patient's nostrils 64, 66, and the nasal tube 58 and cord ends 16a, 16b are secured together using the clip member 18, as is described further below.

Figures 3A, 3B, 4:
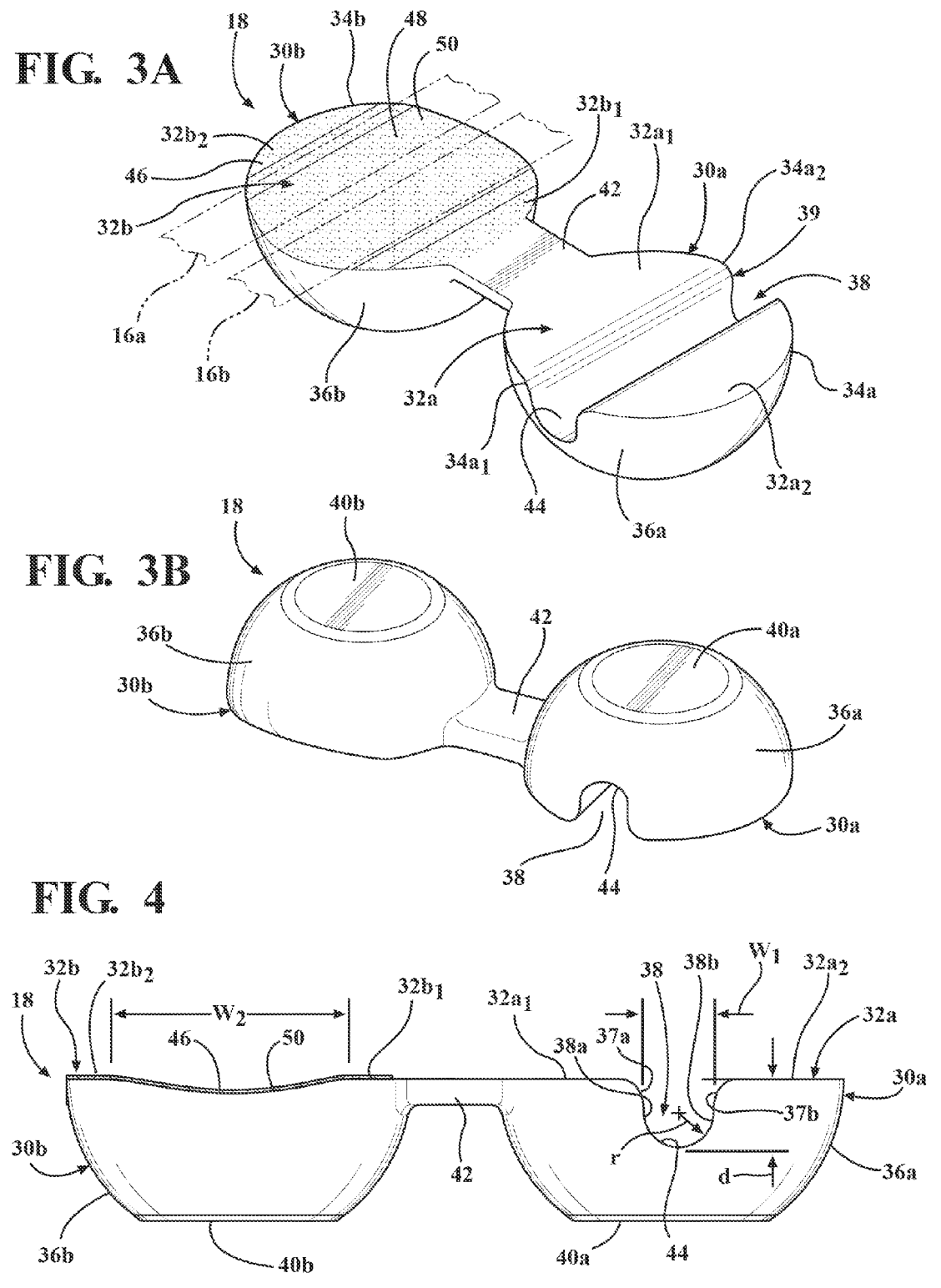

Referring to FIGS. 3A, 3B and 4, the clip member 18 includes first and second pivotally connected clip portions 30a, 30b. Each of the clip portions 30a, 30b include a respective inner mating surface 32a, 32b for mating engagement with the mating surface 32a, 32b of the other clip portion 30a, 30b. The mating surface 32a, 32b of each clip portion 30a, 30b defines a respective generally circular perimeter 34a, 34b at an intersection of the mating surface 32a, 32b with an outer surface 36a, 36b of the clip portion 30a, 30b, wherein the perimeters 34a, 34b define generally similar diameters. Further, the mating surfaces 32a, 32b are at least partially defined by respective planar mating surfaces, wherein the mating surface 32a includes planar mating surfaces $32a_1$ and $32a_2$, and the mating surface 32b includes planar mating surfaces $32b_1$ and $32b_2$.

As seen in FIG. 3A, the first clip portion 30a includes an elongated nasal tube channel 38 extending from the mating surface 32a into the first clip portion 30a. In particular, the channel 38 extends below the mating surface 32a, with the planar mating portions $32a_1$, $32a_2$ extending to either side of the channel 38. The channel 38 extends between diametrically opposite sides $34a_1$, $34a_2$ of the perimeter 34a to provide a passage for the nasal tube 58 (FIG. 7C) through the clip member 18. Further, the edges 37a, 37b formed between the planar mating portions $34a_1$, $34a_2$ and channel walls 38a, 38b are formed as chamfered edges forming a channel opening 39 that is wider than the spacing between the channel walls 38a, 38b to facilitate passage of the nasal tube 58 into the channel 38.

Each of the clip portions 30a, 30b are formed with a generally hemispherical shape, as defined by arcuate surfaces of the respective outer surfaces 36a, 36b. When the mating surfaces 32a, 32b are positioned in mating engagement with each other, the outer surfaces of the clip portions 30a, 30b form a generally spherical shape for the outer surface for the clip member 18. More specifically, as may be seen in FIG. 3B, the outer surfaces 36a, 36b preferably comprise frusto-hemispherical surfaces including respective outer flat surfaces 40a, 40b. That is, the arcuate outer surfaces 36a, 36b end in the outer flat surfaces 40a, 40b to form the clip member 18 with a frusto-spherical shape, including opposing frusto-spherical ends (see FIG. 6).

The clip portions 30a, 30b are formed of a soft elastomeric material and, in accordance with an aspect of the invention, the clip portions 30a, 30b are preferably formed of relatively soft silicone material that flexes resiliently in response to a pressure applied to a surface thereof. Alternatively, the clip portions 30a, 30b may be formed of a soft elastomeric material comprising a soft TPE material. In accordance with a specific example of a relatively soft elastomeric material, the clip portions 30a, 30b are formed of elastomeric material in a durometer Shore A range of 40 or less. Further, the clip portions 30a, 30b are pivotally connected by a hinge portion 42. The hinge portion 42 is integrally formed with the clip portions 30a, 30b, such as during a molding operation forming the clip portions 30a, 30b.

Referring to FIG. 4, the channel 38 is dimensioned with a spacing between the channel walls 38a, 38b that is equal to or about equal to a diameter of the nasal tube 58 such the channel walls 38a, 38b engage against the outside of the nasal tube 58 to form a static friction connection, i.e., a stiction connection, therebetween. The nasal tube 58 may be formed, for example, of polyvinyl chloride (PVC) or polyurethane (PUR). The channel 38 includes a radially inner surface 44 defining a radius, r, that is generally equal to one-half an outer diameter of the nasal tube 58. Further, a depth, d, of the channel 38, as measured from the mating surface 32a to an apex of the inner surface 44 of the channel 38 is generally equal to the width, $w_1$, of the channel 38, as measured between the channel walls 38a, 38b.

It may be understood that the width, $w_1$, of the channel 38 being about equal to the diameter of the nasal tube 58 may include tolerance variations that may increase engagement of the inner surface 44 with the lower or inner half of the nasal tube 58. However, the soft characteristic of the elastomeric material, producing the stiction engagement with the nasal tube 58, is also sufficient to resist movement due to the contact that necessarily occurs along the length of the channel 38 at the radially inner locations engaging the nasal tube 58, i.e., at locations radially inwardly into the channel 38 away from the opening 39. In addition, it may be understood that the opening 39 of the channel 38 is outwardly curved to provide an unobstructed opening that the nasal tube 58 may easily slide into position without catching on portions of the side walls 38a, 38b at the opening 39.

As illustrated in FIGS. 3A and 4, at least one of the first and second clip portions 30a, 30b includes an adhesive coating 46 on a respective mating surface 32a, 32b thereof. Alternatively, the adhesive coating 46 may be provided to both of the mating surfaces 32a, 32b. In the illustrated preferred example, the adhesive coating 46 is applied only to the mating surface 32b of the second clip portion 30b. The adhesive coating 46 creates an immovable or permanent bond between the mating surface 32b of the second clip portion 30b and a portion of the nasal tube 58 surface facing outwardly from the channel 38 when the mating surfaces 32a, 32b are in engagement with each other. Further, the adhesive coating 46 permanently bonds at least the planar mating surfaces $32a_1$, $32a_2$ and $32b_1$, $32b_2$ to each other when the first and second clip portion 30a, 30b are pivoted about the hinge 42 into engagement with each other.

Prior to pivoting closure of the first and second clip portion 30a, 30b into engagement with each other, the first and second ends 16a, 16b of the support cord 16 may be positioned on either side of the channel 38 after the nasal tube 58 is located therein, as is illustrated in FIG. 7C. When the mating surfaces 32a, 32b are brought into engagement with each other, the cord ends 16a, 16b may be adhesively engaged by the adhesive coating 46 and located between the mating surfaces 32a, 32b, to immovably retain the cord ends 16a, 16b in engagement with the clip member 18. It may be understood that, although the cord ends 16a, 16b cover a portion of the adhesive coating 46, such as may be provided on the mating surface 32b, at least a portion of the planar mating surfaces $32b_1$, $32b_2$ will remain uncovered by the cord ends 16a, 16b for engagement with the respective planar mating surfaces $32a_1$, $32a_2$. Also, a central elongated area defined by a longitudinally extending spacing between the cord ends 16a, 16b is preferably provided to permit contact of the adhesive coating 46 with the outer surface of the nasal tube 58.

Further, a central area 48 of the mating surface 32b on the second clip portion 30b may be formed with a shallow elongated indentation 50 for receiving the cord ends 16a, 16b. The elongated indentation has a width, $w_2$, that is contiguous with and extends laterally outwardly from the width, $w_1$, of the channel 38 when the clip portions 30a, 30b are in mating engagement. The elongated indentation 50 is formed with a depth substantially matching a thickness of the cord ends 16a, 16b to thereby permit additional closure of the clip portions 30a, 30b together, with sufficient space in the indentation 50 to accommodate the cord ends 16a, 16b, for more complete contact between the planar mating surfaces $32a_1$, $32a_2$ and $32b_1$, $32b_2$. It may be understood that, within the scope of the invention, an operable embodiment of the clip member 18 may be formed by providing the entire mating surface 32b of the second clip portion 30b as a planar surface, without the indentation 50.

Prior to engagement of the mating surfaces 32a, 32b to permanently affix the clip member to the nasal tube 58 and the cord ends 16a, 16b, the adhesive coating 46 may be covered with a detachable film cover 52. That is, the clip member 18 may initially be provided with a protective film cover 52 over the adhesive coating 46. The film cover 52 may include a tab portion 54 for enabling a user to conveniently grasp the film cover 52 and peel it from engagement on the mating surface 32b to expose the adhesive coating 46.

Figure 6:
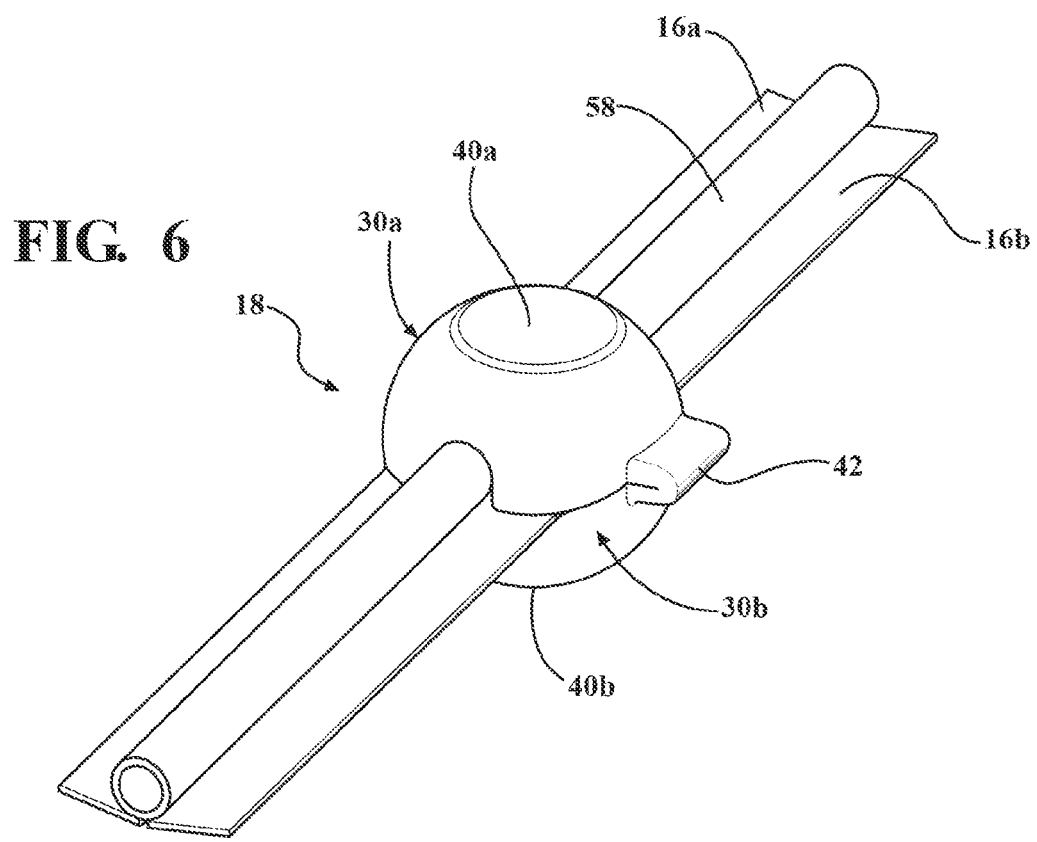
FIG. 6 is a perspective view illustrating the clip member closed over a nasal tube and retention cord ends.

In one example of a use of the clip member 18, subsequent to insertion of the nasal tube 58 into a nostril of the patient, the clip member 18 is positioned onto the nasal tube 58 such that the channel 38 receives the nasal tube 58. The clip member 18 remains in a selected position adjacent to the patient's nostril due to the frictional engagement created between the outer surface of the nasal tube 58 and the soft elastomeric material of the channel walls 38a, 38b. The film cover 52 may then be peeled from the second mating surface 32a, and the cord ends 16a, 16b may be positioned on the adhesive layer 46 at least partly spaced to expose a strip of the adhesive 46 therebetween. The first and second clip portions 30a, 30b may be pivoted together to join the mating surfaces 32a, 32b and to engage the exposed strip of adhesive 46 between the cord ends 16a, 16b with the nasal tube 58, as illustrated in FIG. 6.

In order to form a secure bond between the mating surfaces 32a, 32b, the user applies pressure to the opposing frusto-spherical ends at the outer flat ends 40a, 40b to firmly compress the clip portions 30a, 30b together. The outer flat ends 40a, 40b facilitate stable engagement of the user's fingers with the outer surfaces 36a, 36b of the clip member 18. Further, the frusto-spherical shape of the clip member 18 may have a diameter, e.g., as measured across the perimeters 34a, 34b, of about one-half inch and provides a member that will have a minimum contact surface area with a patient's face below the patient's nose 60. Additionally, the frusto-spherical shape, in combination with the soft elastomeric material, operates such that points of engagement between the clip member 18 and the patient's face comprise rounded soft surfaces, permitting a distribution of pressure at points of contact with the patient's face. Hence, the configuration of the present clip member 18 reduces discomfort that may be associated with other clip constructions by implementing a combination of shape and material, as well as reduced size, to minimize or reduce contact pressure on the patient's face. It may be noted that the size of the clip member 18 is such that it is prevented from entering the patient's nostril, while minimizing the diameter.

Further, the configuration of the clip member 18 facilitates installation by providing a channel which easily slips over the nasal tube 58 and remains in position by frictional engagement. The positioning and retention of the cord ends 16a, 16b in the clip member 18, and closure of the clip member 18, are facilitated by the adhesive coating 46 that may be applied to one or both of the mating surfaces 32a, 32b, enabling a secure installation with a minimum of parts or elements forming the clip member 18.

It may be understood that the clip member 18 may be molded having a channel sized to any tube that is to be used with the clip member 18, and that a variety of clip members 18, having various sized channels 38, as well as various size outer diameters, to accommodate the various tube sizes commonly used, may be provided.

Referring to FIGS. 8A-D, an alternative configuration for the clip member is illustrated. Elements of the clip member 118 of the alternative configuration shown in FIGS. 8A-D and corresponding to the clip member 18 described with reference to FIGS. 3A, 3B, 4 and 5 are labeled with the same reference numerals increased by 100.

The clip member 118 includes first and second pivotally connected clip portions 130a, 130b. Each of the clip portions 130a, 130b include a respective inner mating surface 132a, 132b for mating engagement with the mating surface 132a, 132b of the other clip portion 130a, 130b. The mating surfaces 132a, 132b are at least partially defined by respective planar mating surfaces, wherein the mating surface 132a includes planar mating surfaces $132a_1$ and $132a_2$, and the entire mating surface 132b comprises a planar mating surface. An elongated nasal tube channel 138 extends into the first clip portion 130a between the planar mating surfaces $132a_1$ and $132a_2$ for receiving a nasal tube 58 as described above. The clip portions 130a, 130b are pivotally connected by an integrally formed hinge portion 142.

In the current configuration, an adhesive coating 146 is applied to the second mating surface 132 and may extend across the hinge 142 and the planar mating surface $132a_1$ to the edge of the channel 138. Further, as illustrated in FIG. 8C, a film cover 152 may be provided to cover the adhesive coating 146, and a tab 154 of the film cover 152 extends beyond the planar mating surface $132a_1$ and over the channel 138 to facilitate grasping the film cover 152 for removal during use of the clip member 118.

In accordance with an aspect of the invention, the clip member 118 includes a clasp structure comprising a pin 170 molded on the second clip portion 130b and extending outwardly from the plane of the mating surface 132b, and a pin receiving hole 172 molded in the planar mating surface 132$a_2$. The outer surface 136a of the first clip portion 130a may include a boss 176 to provide additional material on the first clip portion 130a for accommodating the pin receiving hole 172. The pin receiving hole 172 is located on the first clip portion 130a to receive the pin 170 when the first and second clip portions 130a, 130b are in mating engagement with each other.

As may be seen in FIG. 8D, the pin receiving hole 172 may include a circular groove 178 located between an entrance 180 and a bottom 182 of the hole 172. The groove 178 is configured to engage a rib 184 formed on the circumference of the pin 170 to provide a locking engagement between the pin 170 and hole 172 to prevent or substantially resist separation of the mating surfaces 132a, 132b of the first and second clip portions 130a, 130b. It should be understood that the clasp structure formed by the pin 170 and pin receiving hole 172 is provided in addition to the adhesive coating 146 for maintaining the first and second mating surfaces 132a, 132b in engagement with each other.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nasal retention system for securing at least one nasal tube extending through a nose of a patient, the retention system comprising:
a clip member including first and second pivotally connected clip portions, each of said clip portions including a planar inner mating surface for mating engagement with the planar mating surface of the other clip portion;
said planar mating surface of each said clip portion defining a generally circular perimeter at an intersection of said planar mating surface with an outer surface said clip portion; and
said first clip portion including an elongated nasal tube channel extending from said planar surface into said first clip portion, said elongated nasal tube channel extending between diametrically opposite sides of said perimeter of said first clip portion for receiving a nasal tube therethrough when said mating surfaces are in mating engagement with each other;
wherein a depth of said elongated nasal tube channel, extending into said first clip portion from said mating surface, is equal to a width of said channel.

2. The nasal retention system of claim 1, wherein said clip portions are formed of a relatively soft elastomeric material defining an outer surface for the clip member that flexes resiliently in response to pressure applied to a surface thereof.

3. The nasal retention system of claim 2, wherein said soft elastomeric material is a elastomeric material in a durometer Shore A range of 40 or less.

4. The nasal retention system of claim 1, wherein said outer surface of each of said first and second clip portions is defined as a generally hemispherical outer surface.

5. The nasal retention system of claim 4, wherein said clip member, with said mating surfaces in mating engagement, defines a generally spherical member.

6. The nasal retention system of claim 5, including diametrically opposed flat portions formed on each of the generally hemispherical portions defining opposed finger engagement locations.

7. The nasal retention system of claim 5, wherein a diameter defined by an outer surface of said generally spherical member is about ½ inch.

8. The nasal retention system of claim 1, wherein at least one of said first and second clip portions include an adhesive coating for retaining said clip portions in engagement with each other upon contact of said mating surfaces with each other.

9. The nasal retention system of claim 1, including a pin located on one of said first and second clip portions and a hole located on the other of said first and second clip portions, said pin and hole located for engagement with each to maintain said clip portions in engagement with each other when said mating surfaces are in mating engagement with each other.

10. The nasal retention system of claim 1, wherein said elongated nasal tube channel has a radially inner surface, located radially inwardly from said mating surface of said first clip portion.

11. The nasal retention system of claim 1, including engagement surfaces on said mating surfaces for engaging a nasal retention umbilical tape on either side of said elongated nasal tube channel.

12. A nasal retention system for securing at least one nasal tube to a nose of a patient, the nasal retention system provided in combination with a nasal tube extending into a nostril of the nose, said nasal retention system including a support cord extending around a nasal septum of the patient and having opposing ends, each cord end extending from a nostril of the nose, and said nasal retention system including a clip member engaged with the tube and engaged with the ends of the support cord:
said clip member of said nasal retention system including:
first and second pivotally connected clip portions formed of a soft elastomeric material, each of said clip portions including an interior surface defining a planar inner mating surface for mating engagement with the planar mating surface of the other clip portion;
said planar mating surface of each said clip portion defining a generally circular perimeter at an intersection of said planar mating surface with an outer surface said clip portion;
said first clip portion including an elongated nasal tube channel extending from said planar surface into said clip first clip portion, said elongated nasal tube channel extending between diametrically opposite sides of said perimeter of said first clip portion for receiving said nasal tube therethrough; and
at least a portion of said second clip interior surface engaging said nasal tube, and a portion of said interior surfaces of each of said first and second clip portions engaging said ends of said support cord, when said mating surfaces are in mating engagement with each other in an assembled state.

13. The nasal retention system of claim 12, wherein said mating surface of said second clip portion includes an adhesive coating for retaining said clip portions in engagement with each other upon contact of said mating surfaces with each other, and said ends of said support cord extend along said mating surfaces, generally parallel to said elongated nasal tube channel, to retain said support cord in engagement between said first and second clip portions.

14. The nasal retention system of claim 12, wherein said soft elastomeric material is an elastomeric material in a durometer Shore A range of 40 or less.

15. The nasal retention system of claim 12, wherein each of said first and second clip portions define generally hemispherical elements, and said clip member defines a generally spherical shape of a size to prevent entry into a patient's nostril in said assembled state.

16. A nasal retention system for securing at least one nasal tube extending through a nose of a patient, the retention system comprising:
- a clip member including first and second pivotally connected clip portions, each of said clip portions including a planar inner mating surface for mating engagement with the planar mating surface of the other clip portion;
- said planar mating surface of each said clip portion defining a generally circular perimeter at an intersection of said planar mating surface with an outer surface said clip portion; and
- said first clip portion including an elongated nasal tube channel extending from said planar surface into said first clip portion, said elongated nasal tube channel extending between diametrically opposite sides of said perimeter of said first clip portion for receiving a nasal tube therethrough when said mating surfaces are in mating engagement with each other;
- wherein at least one of said first and second clip portions include an adhesive coating for retaining said clip portions in engagement with each other upon contact of said mating surfaces with each other.

* * * * *